United States Patent
Acosta-Zara et al.

(10) Patent No.: US 9,918,934 B2
(45) Date of Patent: Mar. 20, 2018

(54) LINKER-BASED LECITHIN MICROEMULSION DELIVERY VEHICLES

(76) Inventors: Edgar Joel Acosta-Zara, Toronto (CA); Shuhong Yuan, Toronto (CA)

( * ) Notice: Subject to any disclaimer, the term of this patent is extended or adjusted under 35 U.S.C. 154(b) by 1781 days.

(21) Appl. No.: 11/609,460

(22) Filed: Dec. 12, 2006

(65) Prior Publication Data

US 2008/0139392 A1   Jun. 12, 2008

(51) Int. Cl.
| | | |
|---|---|---|
| *B01F 17/14* | (2006.01) | |
| *A61K 9/107* | (2006.01) | |
| *B01F 17/00* | (2006.01) | |
| *A61K 9/00* | (2006.01) | |
| *B01F 3/08* | (2006.01) | |

(52) U.S. Cl.
CPC .......... *A61K 9/1075* (2013.01); *A61K 9/0014* (2013.01); *B01F 17/0064* (2013.01); *A61K 9/0019* (2013.01); *A61K 9/0043* (2013.01); *B01F 2003/0834* (2013.01)

(58) Field of Classification Search
CPC .. A61K 9/1075; A61K 9/0014; A61K 9/0019; A61K 9/0043; B01F 2003/0834; B01F 17/0064
USPC .......................................................... 516/21
See application file for complete search history.

(56) References Cited

U.S. PATENT DOCUMENTS

| | | | |
|---|---|---|---|
| 5,444,041 A * | 8/1995 | Owen et al. ....................... 514/2 | |
| 5,654,337 A | 8/1997 | Roentsch et al. | |
| 5,688,761 A | 11/1997 | Owen et al. | |
| 6,191,105 B1 | 2/2001 | Ekwuribe et al. | |
| 6,602,511 B2 | 8/2003 | von Corswant | |
| 6,638,537 B2 | 10/2003 | Dennis et al. | |
| 2002/0146375 A1 | 10/2002 | Schreiber et al. | |
| 2003/0229010 A1 * | 12/2003 | Ekwuribe ......................... 514/3 | |
| 2006/0165739 A1 * | 7/2006 | Komesvarakul et al. .... 424/401 | |

FOREIGN PATENT DOCUMENTS

| | | |
|---|---|---|
| EP | 1 270 007 A2 | 6/2002 |
| WO | 1993002665 A1 | 2/1993 |
| WO | 1993018752 A1 | 9/1993 |
| WO | 200037042 A1 | 6/2000 |

(Continued)

OTHER PUBLICATIONS

Panayiotis P Constantinides, "Review Lipid Microemulsions for Improving Drug Dissolution and Oral Absorption: Physical and Biopharmaceutical Aspects", Pharmaceutical Research, vol. 12, No. 11, 1995, pp. 1561-1572 (1995—month unavailable).*

(Continued)

*Primary Examiner* — Daniel S Metzmaier
(74) *Attorney, Agent, or Firm* — Eduardo Krupnik

(57) ABSTRACT

The present invention relates to biocompatible microemulsion systems designed for controlled release drug delivery applications formulated with phospholipids such as lecithin (surfactant), a lipophilic additive (linker) containing 9 or more carbons in their alkyl group and hydrophilic-lipophilic balance (HLB) of 5 or less, and a surfactant-like hydrophilic additive (linker) containing between 6 to 9 carbon atoms in their alkyl tail. The combination of linkers and phospholipids produce formulations capable of delivering high concentrations of poorly soluble drugs into epithelial tissue using low surfactant concentrations, with minimum cytotoxic side effects.

29 Claims, 2 Drawing Sheets

Cumulative lidocaine permeation

(56) References Cited

FOREIGN PATENT DOCUMENTS

| WO | WO 2005/092298 A1 | * | 10/2005 |
|---|---|---|---|
| WO | 2006074177 A2 | | 7/2006 |
| WO | 2006097793 A2 | | 9/2006 |

OTHER PUBLICATIONS

Hirotsune Igimi et al, "A useful cholesterol solvent for medical dissolution of gallstones", Journal of Gastroenterology, vol. 27, No. 4 / Aug. 1992, pp. 536-545, obtained online @ http://www.springerlink.com/content/x70rr3jk26r584j4/ (downloaded Jul. 14, 2010).*

CAPTEX® 200, Specification sheet, AIC, Framingham, MA USA, online @ http://www.aicma.com/products/Medium%20Chain%20Trigylceride%20-%20Captex%20200%20CAP200.pdf, (downloaded Mar. 14, 2012), 1 page.*

Alison G Floyd, "Top ten considerations in the development of parenteral emulsions", Pharmaceutical Science & Technology Today vol. 2, Issue 4, Apr. 1, 1999, pp. 134-143.*

Prajapati et al, "A Comparative Evaluation of Mono-, Di- and Triglyceride of Medium Chain Fatty Acids by Lipid/Surfactant/Water Phase Diagram, Solubility Determination and Dispersion Testing for Application in Pharmaceutical Dosage Form Development", Pharm Res (2012) 29:285-305.*

Vandamme, "Microemulsions as ocular drug delivery systems: recent developments and future challenges", Progress in Retinal and Eye Research 21 (2002) 15-34.*

Templer et al., Inverse Bicontinuous Cubic Phases in 2:1 Fatty Acid/Phosphatidylcholine Mixtures. The Effects of Chain Length, Hydration, and Temperature, J. Phys. Chem. B 1998, 102, 7251-7261.*

Acosta, Edgar et al. "The Role of Hydrophilic Linkers," Journal of Surfactants and Detergents, vol. 5, No. 2m pp. 151-157 (Apr. 2002), AOCS Press.

Acosta, Edgar et al. "Linker-Based Bio-compatible Microemulsions," Environmental Science & Technology, vol. 39, No. 5, pp. 1275-1282, 2005, American Chemical Society, Published on the Web Jan. 7, 2005.

Salager, J.L., et al. (2005) Enhancing solubilization in microemulsions—State of the art and current trends. Journal of Surfactants and Detergents, 8(1): 3-21.

Documentation from Opposition for European Patent No. 2120871 dated Feb. 14, 2017.

* cited by examiner

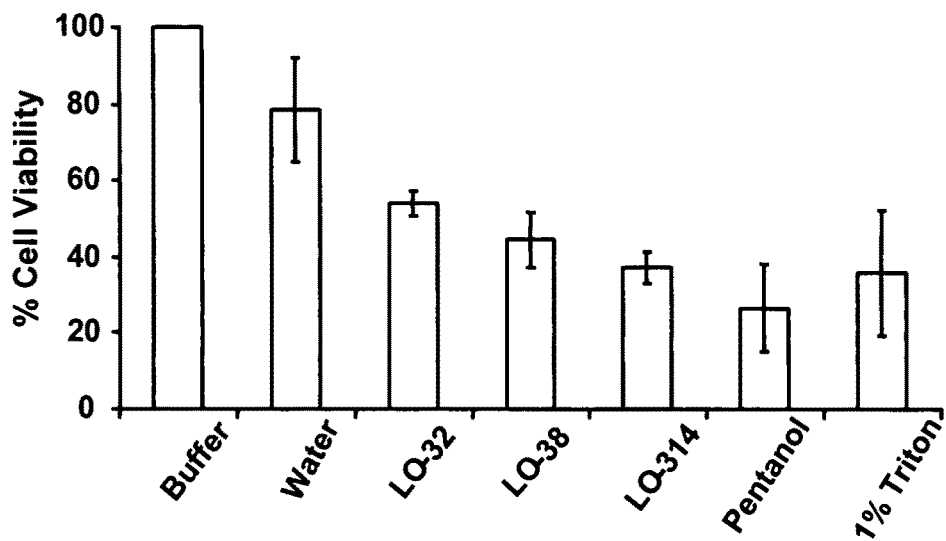
Fig. 1 *In vitro* cytotoxicity of various lidocaine vehicles against MATTEK™ reconstructed human skin
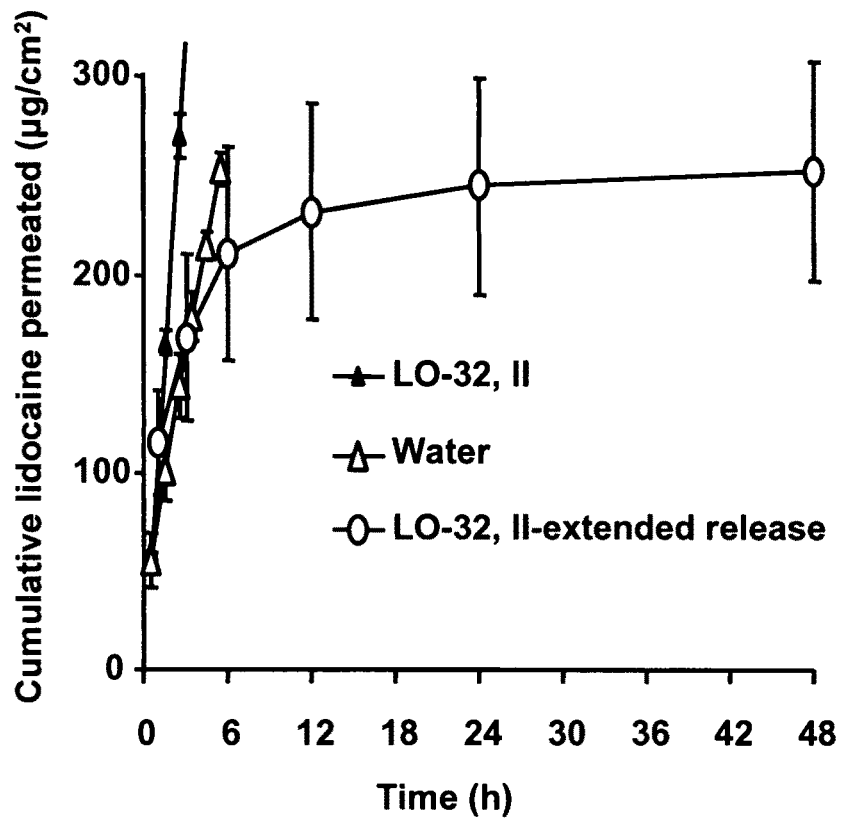
FIG. 2 Cumulative lidocaine permeation

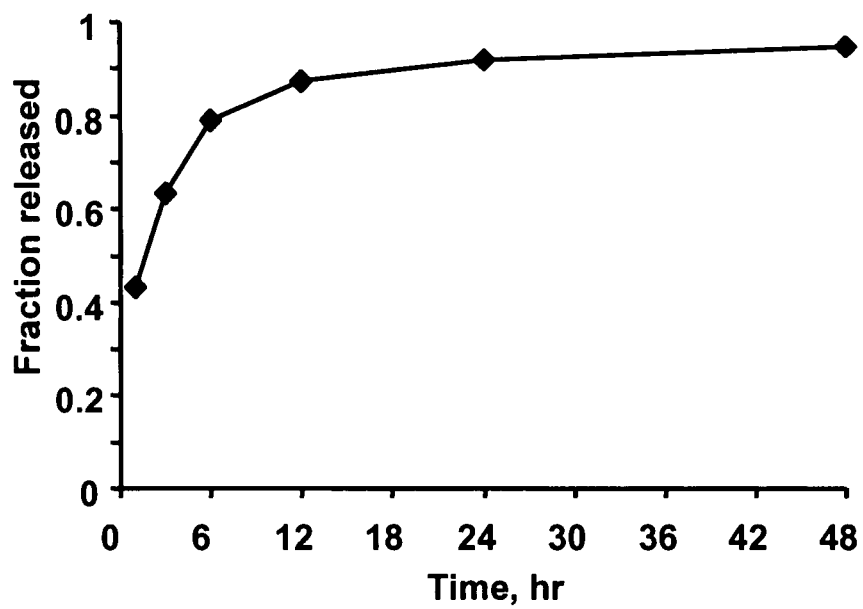
FIG. 3 Fraction of lidocaine released from skin impregnated with formulation LO-32

LINKER-BASED LECITHIN MICROEMULSION DELIVERY VEHICLES

FIELD OF THE INVENTION

The present invention relates to microemulsion systems designed for controlled release drug delivery applications.

BACKGROUND OF THE INVENTION

Microemulsions have many advantages, including: (1) high solubilization capacity of both water-soluble and oil-soluble drugs; (2) thermodynamically stable; (3) transparent; and (4) formed spontaneously without addition of external energy. A 1998 review on the state of the art of microemulsion drug delivery indicates that the major advantages of microemulsions over other systems derives from their ability to increase the solubility of poorly soluble drugs (in water) in the vehicle and increase interfacial area for mass transfer (due to small particle size) resulting in an increase in drug permeability through epithelial tissues (Malmstem, Handbook of Microemulsion Science and Technology. Kumar, P. Ed. Marcell Dekker, Inc.: New York, 1999). In the same review, it is indicated that while nonionic surfactants significantly reduce the toxicity associated with microemulsions, fully non-toxic and biocompatible microemulsions would only be possible when microemulsions could be formulated with natural surfactants (e.g., lecithin) and avoiding the use of short and medium chain alcohols.

In a more recent review (Prausnitz, M. R.; Mitragotri, S. and Langer, R. Nat Rev Drug Discovery, 2004, 3(2):115-24) different drug delivery methods, including surfactant systems, have been compared. The authors indicate that surfactant-based vehicles typically increase drug permeability by solubilizing the lipids and denaturing the keratin of the stratum corneum, leading to an increase in toxic side-effects such as skin erythema and eczema. The authors indicate that new breakthroughs in surfactant-based, and other chemical enhancer formulations would be possible only through a better understanding of the vehicle-drug-skin interactions.

U.S. Pat. No. 5,654,337 to Roentsch et al. describes a formulation used for the delivery of pharmaceutically active agents through the skin. It consists of a biocompatible organic solvent (isopropyl myristate), a polar lipid (lecithin), a surfactant, water and urea. This work produces a "speed-gel" product which is similar to organogels (microemulsion-based gel), but differs from microemulsions in that the speed-gel is meta-stable (due to the high viscosity) and microemulsions are thermodynamically stable and can be formulated having low viscosities, making microemulsions suitable for a wider range of applications.

An oil-in-water microemulsion is described in U.S. Pat. No. 5,688,761 to Owen et al. This microemulsion is suitable for administration of water-soluble protein drugs. By the addition of aqueous fluid, it readily converts an oil-in-water emulsion to a water-in-oil microemulsion and releases the active agent. However, it is ineffective in actual application due to a need of surfactant modifiers to lower the surfactant content to the amount stated in the claims.

U.S. Pat. No. 6,191,105 to Ekwuribe et al. describes a water-in-oil microemulsion with a hydrophilic and lipophilic balance (HLB) value between 3 and 7 is described for oral or parenteral delivery of insulin protein covalently coupled with a polymer. In this particular formulation, the uses of polyethylene glycols or propylene glycols (which increase the viscosity of the formulation and are not readily metabolized) are essential to formulate the microemulsion system.

An oil-in-water or bicontinuous microemulsion is described in U.S. Pat. No. 6,602,511 to von Corswant which is suitable for parenteral, oral and transdermal administration of lipophilic drugs. This system consists of a hydrophilic surfactant, a hydrophobic surfactant (lecithin), a surfactant film modifier, and one or more components for adjusting the polarity of the microemulsion. Such system is said to provide a pharmaceutically acceptable non-toxic vehicle. However, the formulations described in this patent contain 3-13% ethanol which may produce tissue irritation and sensitization after repeated dose. Similar to U.S. Pat. No. 6,191,105 this patent also requires the use of hydrophilic polymers such as polyethylene glycol.

Lastly, U.S. Pat. No. 6,638,537 to Dennis et al., describes an oil-in-water microemulsion for intravenous delivery of oil-soluble drugs. This microemulsion consists of a long polymer chain surfactant and a short fatty acid (C8-C12) surfactant as a co-surfactant. The release rate of a drug from the microemulsion micelles are briefly disclosed by comparing with the commercially available drug preparation. The microemulsion does not contain any alcohol and yet it produces satisfactory results. One problem with the formulation, however, is that it requires at least 25% w/v surfactant to form the microemulsion system which increases viscosity costs, and potential toxic side effects.

It has been found that mixtures of lipophilic linkers such as oleyl alcohol (amphihilic molecules with HLB of 5 or less, and more than 9 carbons in the alkyl group), hydrophilic linkers such as hexyl glucoside (amphiphilic molecules with 6 to 9 carbons in the alkyl group), and lecithin produce microemulsions with a wide range of oils and without the need for short or medium chain alcohols (Acosta, E.; Nguyen, T.; Witthayapanyanon, A.; Harwell, J. H. and Sabatini, D. A. Linker-based bio-compatible microemulsions, Enviro. Sci. Technol. 2005, 39: 1275-1282).

The use of linker microemulsions in drug delivery systems and their cytotoxic effects are not known. What are needed therefore are linker-based lecithin formulations for drug delivery systems that increase drug uptake by an increase of drug absorption in epithelial tissue with minimum cytotoxic side effects.

SUMMARY OF THE INVENTION

The present invention relates to formulation of biocompatible microemulsions as controlled release delivery vehicles for poorly soluble active ingredients in topical, transdermal, oral, transnasal, and intravenous delivery. The formulation is a combination of: (1) lecithin (extracted from soybean or other source); (2) a lipophilic amphiphile with 9 carbon atoms or more in its tail group, and hydrophilic lipophilic balance (HLB) of 5 or less; (3) a hydrophilic amphiphile with an anionic, non-ionic, cationic or zwitterionic head group and tail group containing between 6 to 9 carbon atoms; (4) a carrier or solvent oil (alkyl esters of fatty acids or terpenes) that may be required to dilute the active ingredient; and (5) water. This combination at specific ratios yields thermodynamically stable microemulsions capable of increasing the solubility (in isotonic solutions) of hydrophobic drugs (e.g., lidocaine, or alpha-tocopherol acetate) by more than 20 fold. Such an increase in solubility produces an increase in the absorption and permeation of active ingredients through the epithelial tissue (of humans and animals), and the waxy cuticle of leaves without significant cytotoxic side effects that are typically observed in other surfactant-based vehicles.

Most of the reported formulations using lecithin as surfactant required large concentrations (5% w/w or more) of C2-C6 alcohols or polyethylene glycol as co-solvents. In most cases, however, high concentrations of these co-solvents trigger allergic reactions. The formulations disclosed here do not require the use of such co-solvents.

BRIEF DESCRIPTION OF THE DRAWINGS

A detailed description of the preferred embodiments is provided herein below by way of example only and with reference to the following drawings, in which:

FIG. 1 illustrates the in vitro cytotoxicity of various vehicles to delivery lidocaine through MATTEK™ human skin:

FIG. 2 illustrates cumulative lidocaine permeation; and

FIG. 3 illustrates the fraction of lidocaine released.

In the drawings, one embodiment of the invention is illustrated by way of example. It is to be expressly understood that the description and drawings are only for the purpose of illustration and as an aid to understanding, and are not intended as a definition of the limits of the invention.

DETAILED DESCRIPTION OF THE INVENTION

The present invention relates to lecithin-based microemulsions formulated with hydrophilic and lipophilic linker molecules as delivery vehicles for poorly soluble (in water) active ingredients through topical, transdermal, oral, transnasal, and intravenous routes. It has been found that a combination of defatted soybean-extracted lecithin with a lipophilic linker (amphiphiles containing 9 or more carbons and a HLB of 5 or less) such as sorbitan monooleate, and a hydrophilic linker (amphiphiles containing 6 to 9 carbons) such as partially saponified octanoic acid, can produce oil in water (Type I), water in oil (Type II), and bicontinuous (Type III, IV) microemulsions capable of solubilizing poorly soluble (in water) active ingredients and deliver them to and/or through epithelial tissue with minimum cytotoxic side effects. Such microemulsions are produced in isotonic environments containing sodium chloride, without the need for short (C1 to C3) and/or medium (C4 to C8) chain alcohols, or polymeric additives, and may contain a solvent or pharmaceutically acceptable carrier oil such as esters of fatty acids or essential oils.

The increase in transdermal flux/topical absorption of poorly soluble (in water) active ingredients with linker microemulsions vehicles is a product of (1) an increase in active ingredient solubility, (2) an increase in skin permeability, and (3) an unexpected increase in drug absorption on the skin. Surprisingly, it was found that these linker formulations can increase the absorption of poorly soluble drugs in skin, in many instances by 100% or more compared to other vehicles (water, isopropyl myristate, and lecithin microemulsions formulated with medium chain alcohols) and without causing significant cytotoxic effects. Furthermore, it was also found that, contrary to conventional lecithin microemulsions, water in oil (Type II) linker microemulsions are the best vehicles for poorly soluble (in water) drugs, because of the larger drug absorption and transdermal flux, and lower toxicity when compared to oil in water (Type I), and bicontinuous (Type III or IV) microemulsions. A distinct feature of these oil in water (Type II) formulations is that they can be formulated with as low as 2% w/w lecithin and maintain the same level of skin absorption and transdermal delivery than formulations containing 8% w/w of lecithin.

When Type II lecithin linker microemulsions where used in topical applications of lidocaine (used as example drug), they produced a extended release profile over a 12 hour period, similar to those obtained with transdermal patch formulations.

The formulation of lecithin linker microemulsions requires the use of lecithin as the main emulsifier, in concentration range of 0.1% w/w to 8% w/w. The term lecithin (including lysolecithin) generally refers to compounds or mixtures of phosphatidylcholines and other lipids, and containing at least 90% w/w of mono or di-alkyl phosphatidylcholines, and that can be obtained from animal (e.g., eggs), vegetable (e.g., soybean) sources or obtained through chemical synthesis.

The lipophilic linker helps bridging the phosphatidylcholine molecules to the oil phase, and is used in concentrations of 0.1 to 24% w/w. Lipophilic linkers generally refer to amphiphilic molecules with 9 or more carbon in the alkyl chain, and HLB of 5 or less Examples of lipophilic linkers include alcohols such as dodecyl alcohol, oleyl alcohol, cholesterol; fatty acids such as lauric acid, palmitic acid, oleic acid, omega 6-fatty acids, omega 3-fatty acids; fatty acid esters of polyhydric alcohols (sorbitol, maltitol, xylitol, isomalt, lactitol, erythritol, pentaerythritol, glycerol) such as sorbitan monooleate, glycerol monooleate, and others.

Hydrophilic linkers are amphiphilic compounds that contain between 6 to 9 carbon atoms in their alkyl group, are used in concentrations of 0.1 to 24% w/w and as the name suggests, are highly hydrophilic. The hydrophilic group in these linkers can be anionic (sulfates, sulfonates, phosphates, phosphonates, carboxylates, sulfosuccinates) such as octanoates, octyl sulfonates, dibuthyl sulfosuccinates; nonionic (carboxylic acids, alpha-hydroxy acids, esters of polyhydric alcohols, or glucosides, secondary ethoxylated alcohols, pyrrolidones) such as octanoic acid, 2-hydroxyoctanoic acid, hexyl and octyl polyglucosides, octyl pyrrolidone; cationic (amines, quaternary ammonium salts, amine oxides) such as octylamine; or zwitterionic (alkyl aminopropionic acids, betaines, sulfobetaines, phosphatidylcholines) such as octyl sulfobetaine, dibutyryl phosphatidylcholine; and others.

Carrier (solvent) oil may be required to formulate these microemulsions at a concentration ranging from 0 to 95% w/w. Preferred solvent (carrier oils) include alkyl esters of fatty acids such as isopropyl myristate, ethyl caprate, methyl oleate; terpenes such as limonene, pinene; and mixtures of mono- di- and triglycerides. The carrier oil is used to dissolve the hydrophobic active ingredients in the formulation.

Other necessary ingredients include water (0-90% w/w), and electrolytes such as sodium chloride and mixtures of calcium and sodium chloride to produce isotonic formulations.

Poorly soluble (in water) drugs suitable for delivery with these formulations have typically an aqueous solubility of less than 1% w/w in isotonic solutions at room temperature, and that are soluble in the organic (carrier) solvents described above. The list of suitable drugs include: Perylene, Naphthacene, Chrysene, 3-Methylcholanthrene, 3,4-Benzopyrene, Hexachlorobenzene, Benzanthracene, Etomidate, Triphenylene, Anthracene, Fenbuconazole, Pyrene, Lovastatin, Thioridazine, Clofazimine, Danazol, Folic acid, Fenbufen, Equilin, Equilenin, Chlorpyrifos, Fludioxonil, Danthron, Phenanthrene, Diclofenac, Fenpiclonil, Sulindac, Estriol, alpha-tocopherol, alpha-tocopherol acetate, Fluorene, Estradiol, Indoprofen, Indomethacin, Stanolone, Fenoxycarb, Terfenadine, Dihydroequilenin, Norethisterone, Flufenamic acid, G-BHC (Lindane), Acenaphthene, Iopanoic acid, Glafenine, 17Alpha-ethynylestradiol, Diflunisal, 5-Ethyl-5-nonylbarbiturate, Amitriptyline, 1,3,5-Trichlorobenzene, Haloperidol, Progesterone, Iprodione, Dihydroequilin, Prochlorperazine, Diphenyl, Benperidol, Promethazine, Phenyloin, 5,5-Diphenylbarbiturate, Spironolactone, Naproxen, Perphenazine, Simvastatin, Triazolam, 1,4-Dibromobenzene, Testosterone, Prasterone, Methyltestosterone, Estrone, Oxazepam, Triamterene, 5-Ethyl-5-octylbarbiturate, Fenchlorphos, Tenoxicam, Fenclofenac, Pentazocin, Indapamide, Methyclothiazide, Betamethasone, Mefenamic acid, 1,2,3-Trichlorobenzene, Diuron, Diazepam, Flurbiprofen, Thalidomide, Triamcinolone, Naphthalene, Lorazepam, Dexamethasone, Guanine, Bumetanide, 5-t-Butyl-5-(3-methylbut-2-enyl)barbiturate, Sulfadiazine, Linuron, Atrazine, Melphalan, Nitrofurantoin, Isoproturon, Fluometuron, Chlorthalidone, Deoxycorticosterone, Azathioprine, Fludrocortisone, Ibuprofen, Uric acid, Isoguanine, Zileuton, Nalidixic acid, Strychnine, Carbamazepine, Cortisone, Griseofulvin, Corticosterone, 5-Ethyl-5-heptylbarbiturate, Prednisolone, Metoclopramide, Cyclohexane-spirobarbiturate, Ketoprofen, Morphine, Butamben, Alclofenac, Butylparaben, Hydrocortisone, Dapsone, Cyclopentane-spirobarbiturate, Norfloxacin, Hexethal, Hydroflumethiazide, Khellin, Heptabarbital, Disulfiram, Cycloheptane-spirobarbiturate, Oxamniquine, Brinzolamide, Chlortetracycline, Methaqualone, Phenolphthalein, Praziquantel, Sulpiride, Trimethoprim, Chlorzoxazone, Dichlorprop, Quinidine, Sulfathiazole, Heroin, Quinine, Diatrizoic acid, Reposal, 5,5-Di-i-propylbarbiturate, Epinephrine, Tybamate 6-Hydroxypteridine, Pteridine-7-thiol, Sulfamethoxazole, Hydrochlorothiazide, Thebaine, Pteridine-4-thiol, Phenylbutazone, Primidone, Pteridine-2-thiol, Diosgenin, Cefazolin, Ethyl-4-aminobenzoate (Benzocaine), 5-Methyl-5-(3-methylbut-2-enyl)barbiturate, 5-i-Propyl-5-(3-methylbut-2-enyl)barbiturate, Mitomycin C, Propylparaben, Theobromine, Lomefloxacin, 5,5-Dipropylbarbiturate, Carbofuran, Acetazolamide, Xanthine, Amobarbital, Prostaglandin, Isocarboxazid, Vinbarbital, Allopurinol, Adenine, Pentobarbital, Heptobarbital, Phenacetin, Phenobarbital, Pteridine-4-methyl-thiol, Cyclobutane-spirobarbiturate, 5-Allyl-5-phenylbarbiturate, Ethylparaben, 6-Aminopteridine, 5-Ethyl-5-pentylbarbiturate, Glutethimide, Secbutabarbital, Secobarbital, Iodamide, 4-Aminopteridine, 7-Aminopteridine, 2-Aminopteridine, Hypoxanthine, Cyclobarbital, Sulfamethazine, Busulfan, Cocaine, 5-Aminosalicylic acid, 5-Ethyl-5-(3-methylbut-2-enyl)barbiturate, Propylthiouracil, Chlordiazepoxide, Idobutal, 2-Naphthol, Thiamphenicol, Probarbital, 7-Hydroxypteridine, Atropine, Butalbital, Chloramphenicol, Tetroxoprim, Camphor, Ceftazidime, Propoxur, Talbutal, Minoxidil, p-Aminosalicylic acid, 2-Hydroxypteridine, Hyoscyamine, Cyproheptadine, Cycloethane-spirobarbiturate, Salicylamide, L-DOPA, Meprobamate, 7-Butyltheophylline, Salicylic acid, Allobarbital, Lidocaine, Pteridine-2-methyl-thiol, 7-Butyl-8-methyltheophylline, 5,5-Dimethylbarbiturate, Aspirin, Adenosine, Saccharin, Azintamide, Aprobarbital, Methyl-p-hydroxybenzoate, Disopyramide, Tropicamide, Baclofen, Butobarbitone (Butethal), Cyclopropane-spirobarbiturate, Aztreonam, 1-Butyltheobromine, 5-Ethyl-5-allylbarbiturate, Cimetidine, 7-Isobutyl-8-methyltheophylline, Benzoic acid, Pteridine-7-methyl-thiol, Benzoyl peroxide, Butylated hydroxyanisole (BHA), Butylated hydroxytoluene (BHT), Retinol (vitamin A), Carotenoids (lycopene, lutein, carotenes, eugenol).

Because microemulsions are systems in thermodynamic equilibrium, the degrees of freedom of the formulation are set by the phase rule. At a given temperature and pressure, these formulations have a number of ingredients−2 degrees of freedom. To obtain the desired formulation it is required to fix the concentration of lecithin the concentration of one of the linkers (typically the lipophilic one), the electrolyte concentration, the oil/water volume ratio (typically 1:1) and total volume. Then, the concentration of the remaining linker (typically the hydrophilic one) is systematically increased (in different test tubes) to produce a phase scan. With increasing hydrophilic linker concentration, the system undergoes the phase transition Type II (water in oil) to Type III or IV (bicontinuous) to Type I systems (oil in water). The required concentration of hydrophilic linker is therefore determined by the type of microemulsion (Type I, III-IV, II) suitable for the particular delivery application. The preferred hydrophilic linker is a mixture of octanoic acid and sodium octanoate. Because each phase uptakes different levels of oil and water, the final formulation composition is obtained by mass balance (of oil or water) after phase separation.

The concentration of lecithin can be varied according the particular needs of the delivery system, and is typically selected between 0.1% w/w wt. to 8% w/w. Concentrations below this range have poor drug solubility and above this range tend to form undesirable liquid crystal phases. The optimum level for Type II microemulsions is around 2% w/w lecithin and 6% w/w for Type I and Type IV microemulsions. The concentration of lipophilic linker can also vary according to the specific needs of the formulation vehicle. In order to facilitate the formation of clear microemulsion phases, the mass ratio of lipophilic linker to lecithin is kept between 1:1 and 3:1. The preferred ratio is 3:1, and the preferred lipophilic linkers are sorbitan monooleate, glycerol monooleate, and oleic acid.

While all Types of microemulsions produce some level of enhancement of drug delivery to or through epithelial tissue, water in oil (Type II) microemulsions close to transition into bicontinuous (Type III, IV) microemulsions, and bicontinuous (Type IV) microemulsions are preferred due to the maximum drug absorption and transdermal flux with minimum cytotoxic side effects. For selected applications, such as oral and intravenous delivery, oil in water (Type I) microemulsion systems is the preferred form of the formulation.

The formulations disclosed can be used as drug delivery vehicles in transdermal and topical applications, as well as in oral, transnasal, and intravenous applications. The preferred field of application is via transdermal and topical applications. The low viscosity of these formulations (4 to 40 cp) allow them to be used in spray, roll-on, foam, and gel products when viscosity modifying agents such as xanthan gum or carboxyethyl cellulose are added. The aggregate size (oil-swollen micelles or water-swollen reverse micelles) of these formulations ranges from 3 to 10 nm, which makes these formulations optically transparent, of high interfacial area, and capable of permeating through intestinal and alveoli epithelia.

Additionally, the disclosed formulations could be used as permeation enhancers and wetting agents for the delivery of agrochemicals through the waxy cuticle of plant leaves.

In general, the advantages of microemulsion formulations over conventional solvent carriers such as polyethylene glycol are a significant increase in oil solubilization due to the presence of an oil co-solvent, and the presence of surface active molecules that act as permeation enhancing agents. Most surfactants and short and medium chain alcohol co-surfactants increase skin permeability by solubilizing some of the lipid components of the stratum corneum. This lipid solubilization process allows various components, including the surfactant itself to permeate through the skin. Because common anionic surfactants and alcohols trigger cytokine response, traditional formulations tend to produce skin irritation and sensitization. The use of a natural lipid like lecithin, the lack of medium and short chain alcohol, and the use of vegetable oil-derived linkers and solvent oil makes the formulation milder towards epithelial cells. As shown in example 6 and FIG. 1, Types, I, II, and IV linker microemulsions has viability superior to 35% after 5.5 hours of exposure (surpassing the European standards of mildness—skin corrosivity). This is remarkable considering that these formulations contain up to 30% total surfactant content and up to 8% lidocaine. To put these results in context, it is necessary to clarify that the bar labelled as "water" in FIG. 1 contains an isotonic solution with 0.4% lidocaine. In other words, 20 times more lidocaine (which is cytotoxic) was able to be solubilized in the microemulsion system, without compromising the mildness of the formulation.

A surprising new mechanism of drug absorption/delivery was found for these lecithin-linker microemulsions, by which the linker-lecithin combination is absorbed in the epithelial tissue (without "dissolving" the cellular structure), carrying with it high concentrations of active ingredients. In fact, linker lecithin microemulsions show a relatively poor increase in skin permeability (a 2 fold increase) compared to conventional surfactant-based delivery systems (a 10 fold increase or more), but produce partitioning increase into skin of 3 to 4 fold when compared to the solvent oil alone.

The combination of increased microemulsion and active ingredient absorption on the skin and a relatively low increase in skin permeability (low citotoxicity), yields an overall "concealed" delivery effect that can be used as a controlled release mechanism. It has been confirmed that the present microemulsion formulations incorporating a topical dosage will slowly release the drug during a 12 hour period, similar to the delivery profile of transdermal patch products. The advantage of this concealed delivery method over traditional patches are the ability to tailor the dosage (skin area applied), lower cost, avoiding the use of adhesives, invisible application (the lecithin-linker formulations are transparent, and do not produce oily residue), and flexibility of application (the formulation can be used in almost any part of the body).

Linkers with lecithin and an oil solvent may be combined with varying ratios to provide a full range of compositions that will exhibit varying hydrophobicity and polarity. In essence this implies that the physical properties of the microemulsion delivery vehicle we describe is 'programmable'. The solvent oil produces an appropriate environment to solubilize highly hydrophobic/lipophilic non-polar drugs; the lipophilic linker provides a suitable environment to solubilize hydrophobic but polar molecules; the phospholipid surfactant brings all of the environments together and facilitates the solubilization of surface active drugs. Additionally, the phospholipids surfactant acts as a bioadhesive to improve the absorption on epithelial tissue. Finally, more hydrophilic drugs find a suitable solubilization locus around the hydrophilic linkers and water molecules. This gives the linker microemulsions a broad spectrum of application as delivery vehicles for active ingredients.

Another surprising finding about these linker microemulsions is that Type II microemulsions were determined to be the best systems for poorly soluble (in water) drugs such as lidocaine. According to previous reports for conventional (non-linker) microemulsions, lidocaine is best transdermally delivered using Type I (oil in water) microemulsions. For lecithin-linker formulations Type II (water in oil) microemulsions show superior drug solubilization capacity, superior skin permeability, superior drug absorption and lower cytotoxic effects than its Type I counterpart.

EXAMPLES

Example 1. Lidocaine-Ispropyl Myristate Formulation

In these formulations, soybean-extracted lecithin was used as principal surfactant, at a concentration of 8% w/w in the initial aqueous solution. Sodium octanoate and octanoic acid were used as the hydrophilic linkers. The initial aqueous concentration of octanoic acid was 6% w/w. The initial aqueous concentration of sodium octanoate was increased from 1% w/w to 14% w/w at intervals of 1% w/w in each test tube. Sorbitan monooleate (Span 80) served as the lipophilic linker, and used at an initial aqueous concentration of 24% w/w. These microemulsion formulations were formed spontaneously by mixing appropriate quantities of the components with gentle mixing at room temperature. All microemulsion systems were thoroughly vortexed and allowed to equilibrate at 37° C. for at least two weeks, to allow phase equilibrium. A conventional Type II microemulsion formulation (P) with pentanol as a cosurfactant instead of linkers was also generated to compare conventional formulations with linker-based formulations.

Phase behavior studies were performed by mixing 5 mL of aqueous solution (composition described above) and 5 mL of 10% w/w lidocaine solution in isopropyl myristate. Sodium octanoate scans were conducted by varying the sodium octanoate concentration, at constant temperature, aqueous electrolyte concentration (0.9% NaCl) and pressure (1 atm). The phase volumes were determined by measuring the heights of each phase in the test tube. Lidocaine (as example drug) was pre-dissolved in isopropyl myristate (IPM) to a concentration of 10% w/w.

The viscosity of drug loaded microemulsions was measured using a CV-2200 Falling Ball viscometer (Gilmont Instruments, Barrington, Ill., U.S.A.) at room temperature.

The mean droplet size of o/w and w/o microemulsion were determined at 25° C. by a BI-200SM dynamic laser light scattering (Brookhaven Instruments Corporation, Holtsville, N.Y., U.S.A.). Measurements were performed at permanent angle of 90°.

Lidocaine concentration in each phase was quantified by high pressure liquid chromatography (Shimadzu model HPLC, PerkinElmer LC235C Diode Array Detector, SIL-10AP auto-sampler with a 20 µl loop, 200 LC pump, Class D-7500 integration software) on a reverse phase column (Genesis, C18, 4 µm, 150×4.6 mm). The mobile phase consisted of acetonitrile-0.05 M NaH2PO4 (30:70, v/v) and the measurement was conducted under isocratic condition (1.0 mL/min) by detection at 230 nm. The retention time of lidocaine under these conditions was between 2.0 and 3.0 min. The peak area correlated linearly with lidocaine concentrations in the range 100-1000 µg/mL.

Table 1 summarizes the composition, microemulsion type, phase volumes, viscosity and drop size of microemulsion aggregates. (Where: (a) is lecithin; (b) is sorbitan monooleate; (c) is octanoic acid; (d) is sodium octanoate; (e) is water; (f) is lidocaine; (g) is isopropyl myristate; and (v) is microemulsion volume. Concentrations are expressed on a weight percentage basis (w/w).)

TABLE 1

Composition and properties of lidocaine-isopropyl myristate microemulsions.

| Series # | % (a) | % (b) | % (c) | % (d) | % (e) | % (f) | % (g) | Type | Viscosity cP | Size nm | (v). ml |
|---|---|---|---|---|---|---|---|---|---|---|---|
| LO-31 | 6.8 | 20.5 | 5.1 | 0.9 | 1.8 | 5.8 | 64.9 | II | 11 +/− 1 | 6 +/− 1 | 5.9 |
| LO-32 | 6.5 | 19.5 | 4.9 | 1.6 | 5.6 | 5.9 | 61.9 | II | 14 +/− 1 | 7 +/− 1 | 6.1 |
| LO-33 | 6.2 | 18.7 | 4.7 | 2.3 | 9.0 | 6.0 | 59.1 | II | 14 +/− 1 | 8 +/− 1 | 6.4 |
| LO-34 | 6.0 | 17.9 | 4.5 | 3.0 | 12.1 | 6.0 | 56.6 | II | 17 +/− 1 | 8 +/− 1 | 6.7 |
| LO-35 | 5.6 | 16.8 | 4.2 | 3.5 | 16.7 | 6.1 | 53.2 | II | 21 +/− 2 | 8 +/− 1 | 7.1 |
| LO-36 | 5.0 | 15.0 | 3.8 | 3.8 | 25.0 | 5.7 | 47.5 | II | 27 +/− 3 | 9 +/− 1 | 8.0 |
| LO-37 | 4.0 | 12.0 | 3.0 | 3.5 | 39.5 | 5.4 | 38.0 | II | 30 +/− 4 | 9 +/− 1 | 10.0 |
| LO-38 | 4.0 | 12.0 | 3.0 | 4.0 | 27.0 | 5.0 | 50.0 | IV | 22 +/− 2 | 8 +/− 1 | 10.0 |
| LO-39 | 4.4 | 13.1 | 3.3 | 4.9 | 29.0 | 5.0 | 45.3 | IV | 27 +/− 5 | 8 +/− 1 | 9.1 |
| LO-310 | 5.2 | 15.6 | 3.9 | 6.5 | 33.7 | 4.8 | 35.2 | I | 31 +/− 3 | 10 +/− 1 | 7.7 |
| LO-311 | 5.4 | 16.2 | 4.0 | 7.4 | 34.3 | 4.5 | 32.7 | I | 37 +/− 3 | 9 +/− 1 | 7.4 |
| LO-312 | 5.6 | 16.8 | 4.2 | 8.4 | 35.0 | 4.3 | 30.0 | I | 36 +/− 4 | 8 +/− 1 | 7.1 |
| LO-313 | 5.8 | 17.5 | 4.4 | 9.5 | 35.7 | 4.3 | 27.1 | I | 35 +/− 3 | 8 +/− 1 | 6.9 |
| LO-314 | 6.1 | 18.3 | 4.6 | 10.7 | 36.5 | 4.1 | 23.9 | I | 33 +/− 2 | 8 +/− 1 | 6.6 |

Example 2. Lidocaine-Ethyl Caprate Formulation

The same formulation procedure of Example 1 was used, except that the carrier oil, isopropyl myristate was replaced by ethyl caprate. Table 2 summarizes the composition and properties of these formulations. (Where: (a) is lecithin; (b) is sorbitan monooleate; (c) is octanoic acid; (d) is sodium octanoate; (e) is water; (f) is lidocaine; (g) is ethyl caprate; and (v) is microemulsion volume. Concentrations are expressed on a weight percentage basis (w/w).)

TABLE 2

Composition and properties of lidocaine-ethyl caprate microemulsions.

| Series # | % (a) | % (b) | % (c) | % (d) | % (e) | % (f) | % (g) | Type | Viscosity cP | (v). ml |
|---|---|---|---|---|---|---|---|---|---|---|
| LE-83 | 6.4 | 19.1 | 4.77 | 2.4 | 6.9 | 7.7 | 52.7 | II | | 6.3 |
| LE-84 | 6.2 | 18.7 | 4.67 | 3.1 | 8.2 | 7.6 | 51.6 | II | 7 +/− 1 | 6.4 |
| LE-85 | 5.8 | 17.5 | 4.38 | 3.6 | 13.2 | 7.1 | 48.3 | II | | 6.9 |
| LE-86 | 5.7 | 17.1 | 4.29 | 4.3 | 14.3 | 7.0 | 47.3 | II | | 7.0 |
| LE-87 | 5.3 | 15.8 | 3.96 | 4.6 | 20.1 | 6.5 | 43.7 | II | 16 +/− 2 | 7.6 |
| LE-88 | 4.0 | 12.0 | 3.00 | 4.0 | 39.0 | 5.0 | 33.0 | IV | | 10.0 |
| LE-89 | 4.0 | 12.0 | 3.00 | 4.5 | 38.5 | 5.0 | 33.0 | IV | 22 +/− 4 | 10.0 |
| LE-810 | 4.0 | 12.0 | 3.00 | 5.0 | 38.0 | 5.0 | 33.0 | IV | | 10.0 |
| LE-811 | 4.4 | 13.1 | 3.28 | 6.0 | 41.0 | 5.0 | 27.2 | I | 33 +/− 5 | 9.1 |
| LE-812 | 4.7 | 14.0 | 3.50 | 7.0 | 43.2 | 5.0 | 22.7 | I | | 8.6 |
| LE-813 | 4.8 | 14.5 | 3.62 | 7.8 | 44.1 | 4.9 | 20.3 | I | | 8.3 |
| LE-814 | 5.4 | 16.2 | 4.04 | 9.4 | 48.5 | 4.8 | 11.7 | I | 38 +/− 4 | 7.4 |

Example 3. Lidocaine-Isopropyl Myristate (IPM) Using Glycerol Monooleate as Lipophilic Linker The same formulation procedure of Example 1 was used, except that the lipophilic linker, sorbitan monooleate (Span 80) was replaced by glycerol monooleate. (Where: (a) is lecithin; (b) is glycerol monooleate; (c) is octanoic acid; (d) is sodium octanoate; (e)—is water; (f) is lidocaine; (g) is isopropyl myristate; and (v) is microemulsion volume. Concentrations are expressed on a weight percentage basis (w/w).)

TABLE 3

Composition and properties of lidocaine-IPM + glycerol monooleate formulation.

| Series # | % (a) | % (b) | % (c) | % (d) | % (e) | % (f) | % (g) | Type | (v). ml |
|---|---|---|---|---|---|---|---|---|---|
| GM-1 | 5.8 | 17.4 | 4.35 | 0.7 | 16.7 | 7.1 | 48.0 | II | 6.9 |
| GM-2 | 6.3 | 19.0 | 4.76 | 1.6 | 7.9 | 7.7 | 52.6 | II | 6.3 |
| GM-3 | 5.9 | 17.6 | 4.41 | 2.2 | 14.0 | 7.2 | 48.7 | II | 6.8 |
| GM-4 | 5.5 | 16.4 | 4.11 | 2.7 | 19.2 | 6.7 | 45.4 | II | 7.3 |
| GM-5 | 5.1 | 15.2 | 3.80 | 3.2 | 24.7 | 6.2 | 41.9 | II | 7.9 |
| GM-6 | 4.7 | 14.1 | 3.53 | 3.5 | 29.4 | 5.8 | 38.9 | II | 8.5 |
| GM-7 | 4.0 | 12.0 | 3.00 | 3.5 | 39.5 | 5.0 | 33.0 | IV | 10.0 |
| GM-8 | 4.0 | 12.0 | 3.00 | 4.0 | 39.0 | 5.0 | 33.0 | IV | 10.0 |
| GM-9 | 4.7 | 14.0 | 3.49 | 5.2 | 44.8 | 5.0 | 22.9 | I | 8.6 |
| GM-10 | 4.9 | 14.8 | 3.70 | 6.2 | 46.9 | 5.1 | 18.4 | I | 8.1 |
| GM-11 | 5.2 | 15.6 | 3.90 | 7.1 | 48.7 | 5.0 | 14.5 | I | 7.7 |
| GM-12 | 5.5 | 16.4 | 4.11 | 8.2 | 50.7 | 4.8 | 10.3 | I | 7.3 |
| GM-13 | 5.7 | 17.1 | 4.29 | 9.3 | 52.1 | 4.6 | 6.8 | I | 7 |
| GM-14 | 6.0 | 17.9 | 4.48 | 10.4 | 53.7 | 4.0 | 3.5 | I | 6.7 |

Example 4. α-Tocopherol Acetate (a Form of Vitamin E)-Isopropyl Myristate (IPM) Formulation The same formulation procedure of Example 1 was used, except that the active ingredient (lidocaine) was replaced a highly hydrophobic α-tocopherol acetate. (Where: (a) is lecithin; (b) is sorbitan monooleate; (c) is octanoic acid; (d) is sodium octanoatel; (e) is water; (f) is α-Tocopherol Acetate; (g) is isopropyl myristate; and (v) is microemulsion volume. Concentrations are expressed on a weight percentage basis (w/w).)

TABLE 4

Composition and properties of tocopherol acetate-IPM formulation.

| Series # | % (a) | % (b) | % (c) | % (d) | % (e) | % (f) | % (g) | Type | (v). ml |
|---|---|---|---|---|---|---|---|---|---|
| LO-56 | 5.7 | 17.2 | 4.31 | 4.3 | 13.8 | 7.2 | 47.4 | II | 7.0 |
| LO-57 | 5.5 | 16.5 | 4.12 | 4.8 | 16.8 | 6.9 | 45.4 | II | 7.3 |
| LO-58 | 5.2 | 15.5 | 3.87 | 5.2 | 21.3 | 6.5 | 42.6 | II | 7.8 |
| LO-59 | 4.6 | 13.9 | 3.47 | 5.2 | 28.8 | 5.8 | 38.2 | II | 8.6 |
| LO-510 | 4.0 | 12.0 | 3.00 | 5.0 | 38.0 | 5.0 | 33.0 | IV | 10.0 |
| LO-511 | 4.0 | 12.0 | 3.00 | 5.5 | 37.5 | 5.0 | 33.0 | IV | 10.0 |
| LO-512 | 5.5 | 16.5 | 4.14 | 8.3 | 51.0 | 3.1 | 11.4 | I | 7.3 |
| LO-513 | 5.7 | 17.1 | 4.27 | 9.3 | 52.0 | 2.9 | 8.8 | I | 7.0 |
| LO-514 | 5.9 | 17.6 | 4.39 | 10.2 | 52.7 | 2.7 | 6.6 | I | 6.8 |

Example 5. Lidocaine In-Vitro Permeation Studies of Lecithin-Linker Formulations Lidocaine permeability was measured in vitro through reconstructed human skin EpiDerm™ EPI-200 and dorsal pig ear skin using selected formulations of examples 1 through 3. The model skin was placed in a commercial MATTEK™ Permeation Device (MPD). A test formulation (0.4 mL) was applied in the donor compartment. The receptor compartment was filled with 5 mL of PBS (0.01M phosphate, 0.137M NaCl, pH 7.4). At predetermined time, the receiver solution was withdrawn completely from the receptor compartment and was immediately replaced by fresh buffer solution. Sink conditions were maintained at all times. At 5.5 h, the experiment was terminated. All permeation experiments were conducted in triplicate at room temperature.

In addition to selected formulations of examples 1-3, three other formulations were evaluated for benchmark purposes, these include:

1) Water only: distilled water was loaded with 4000 mg/L of lidocaine (saturated conditions).
2) IPM only: isopropyl myristate containing 10% w/w lidocaine.
3) EC only: ethyl caprate containing 10% w/w lidocaine.
4) Pentanol microemulsion: 5.7% w/w lecithin, 17.2% w/w sorbitan monooleate, 11.5% w/w pentanol, 10.9% w/w water (containing 0.9% w/w NaCl), 7.2% w/w lidocaine, 47% w/w isopropanol.

Lidocaine in donor solutions was quantified by high pressure liquid chromatography (Shimadzu model HPLC, PerkinElmer LC235C Diode Array Detector, SIL-10AP auto-sampler with a 20 μl loop, 200 LC pump, Class D-7500 integration software) on a reverse phase column (Genesis, C18, 4 μm, 150×4.6 mm). The mobile phase consisted of acetonitrile-0.05 M NaH2PO4 (30:70, v/v) and the measurement was conducted under isocratic condition (1.0 mL/min) by detection at 230 nm. The retention time of lidocaine under these conditions was between 2.0 and 3.0 min. The peak area correlated linearly with lidocaine concentrations in the range 100-1000 μg/mL.

Lidocaine in receiver solutions was assayed by a UV spectrophotometer (ULTRASPEC PLUS™, Amersham Pharmacia Biotech, U.S.A.). Receiver solutions were diluted with methanol and the absorbance at 230 nm were measured. A linear calibration curve for lidocaine was obtained at 230 nm in a range of 0-100 μg/mL with a linearity of 0.999.

The cumulative lidocaine amount permeated across the skin was plotted as a function of time (h), and average steady-state flux (J, μg/h/cm2) was calculated by dividing the slope from the linear part of the curve by the area of the exposed skin surface (0.256 cm2). Table 5 presents a summary of lidocaine flux obtained for different formulations through MATTEK™ and pig ear skin.

To measure the concentration of lidocaine in pig ear skin, the tissue was removed from the MATTEK™ permeation device, rinse with PBS solution and blotted with lint-free paper tissue to remove any excess of fluid. The tissue was immersed in 2 mL of methanol for a period of 24 hr. After that time, the concentration of lidocaine was measured using the HPLC method described above. The mass of lidocaine extracted is divided by the volume of the tissue (tissue thickness*cross sectional area) to obtain the equivalent lidocaine concentration in the skin. The skin permeability is calculated by dividing the transdermal flux by the lidocaine skin concentration.

TABLE 5

Lidocaine transdermal flux, skin concentration, and skin permeability of selected formulations.

| Formulation | Microemulsion Type | Lidocaine content, % w/w | MatTek ™ Flux μg/hr-cm² | Pig ear skin Flux μg/hr-cm² | Pig ear skin Lidocaine in skin, μg/ml | Pig skin permeability μm/hr |
|---|---|---|---|---|---|---|
| Water | N.A. | 0.4 | 320 +/− 20 | 110 +/− 10 | 6800 +/− 400 | 160 +/− 20 |
| Pentanol | II | 7.0 | 160 +/− 10 | 130 +/− 20 | 5800 +/− 200 | 220 +/− 20 |
| IPM | N.A. | 10.0 | 310 +/− 20 | 140 +/− 10 | 8400 +/− 200 | 170/−20 |
| LO-32 | II | 5.9 | 550 +/− 20 | 420 +/− 40 | 12300 +/− 200 | 340 +/− 30 |
| LO-38 | IV | 5.0 | 460 +/− 20 | 340 +/− 20 | 13500 +/− 300 | 250 +/− 20 |
| LO-314 | I | 4.1 | 310 +/− 30 | 150 +/− 20 | 9500 +/− 200 | 170 +/− 20 |
| EC | N.A. | 5.0 | N.D. | 110 +/− 20 | 4000 +/− 200 | 270 +/− 20 |
| LEC-83 | II | 7.7 | N.D. | 400 +/− 20 | 8300 +/− 200 | 480 +/− 30 |
| LEC-88 | IV | 5.0 | N.D. | 260 +/− 20 | 7600 +/− 200 | 340 +/− 20 |
| LEC-814 | I | 4.8 | N.D. | 150 +/− 20 | 5000 +/− 200 | 300 +/− 30 |
| GM-2 | II | 7.7 | N.D. | 230 +/− 20 | N.D. | N.D. |

TABLE 5-continued

Lidocaine transdermal flux, skin concentration, and skin permeability of selected formulations.

| Formulation | Microemulsion Type | Lidocaine content, % w/w | MatTek ™ Flux µg/hr-cm² | Pig ear skin Flux µg/hr-cm² | Pig ear skin Lidocaine in skin, µg/ml | Pig skin permeability µm/hr |
|---|---|---|---|---|---|---|
| GM-8  | IV | 5.0 | N.D. | 150 +/− 20 | N.D. | N.D. |
| GM-14 | I  | 4.0 | N.D. | 100 +/− 30 | N.D. | N.D. |

Example 6. Cytotoxicity of Lidocaine Formulations

The cell viability assay was performed on the reconstructed human skin EPIDERM™ EPI-200 as described in the standard MATTEK™'s MTT-ET-50. This method is commonly used and established based on reduction of the yellowish MTT to an insoluble purple formazan by active mitochondrial dehydrogenases of living cells. At the end of the exposure period (5.5 h) in the permeation studies, the EPIDERM™ skin model was removed from the MPD, and incubated with 1 mg/ml MTT for 3 h to form formazan. The water-insoluble formazan was then extracted and analyzed spectrophotometrically. In this assay, 1% (w/v) TRITON™ X-100 was used as the positive control and PBS was used as a negative (non-toxic) control. The relative viability can be calculated as the ratio of optical density of the extracted sample divided by the optical density of the negative control.

FIG. 1 presents a summary of the cell viability obtained for selected formulations evaluated in Example 5.

Example 7. Lecithin Dose-Response Curve for Lidocaine Delivery in Linker Microemulsions The formulation LO-32 (a Type II lecithin linker microemulsion) was reformulated using lower lecithin concentration. The transdermal flux through pig ear dorsal skin was also evaluated for selected formulations, and following the procedures described above. Table 6 summarizes these findings. (Where: (a) is lecithin; (b) is sorbitan monooleate; (c) is octanoic acid; (d) is sodium octanoate; (e) is water; (f) is lidocaine; (g) is isopropyl myristate; and (v) is microemulsion volume. Concentrations are expressed on a weight percentage basis (w/w).)

TABLE 6

Lecithin linker lidocaine Type II microemulsions with low lecithin content: formulation and lidocaine transdermal flux through excised pig ear skin.

| Series # | % (a) | % (b) | % (c) | % (d) | % (e) | % (f) | % (g) | (v), ml | Flux µg/cm² |
|---|---|---|---|---|---|---|---|---|---|
| IPM       |     |      |     |     |     | 10  | 90   | 5.1 | 130 +/− 10 |
| LO-32-10  | 0.7 | 2.0  | 0.5 | 0.8 | 0.6 | 8.3 | 87.2 | 5.1 | 200 +/− 10 |
| LO-32-30  | 2.0 | 5.9  | 1.5 | 0.9 | 1.7 | 7.9 | 80.2 | 5.3 | 330 +/− 10 |
| LO-32-60  | 3.9 | 11.7 | 2.9 | 1.2 | 3.3 | 7.5 | 69.4 | 5.7 | 400 +/− 20 |
| LO-32-70  | 4.6 | 13.7 | 3.4 | 1.3 | 3.9 | 7.3 | 65.8 | 5.8 | 400 +/− 10 |
| LO-32-80  | 5.2 | 15.6 | 3.9 | 1.4 | 4.5 | 7.2 | 62.2 | 5.9 | 400 +/− 20 |
| LO-32-100 | 6.5 | 19.5 | 4.9 | 1.6 | 5.6 | 6.8 | 55.1 | 6.2 | 420 +/− 40 |

A similar dilution and evaluation procedure was used for LO-314 (a Type I linker microemulsion). Table 7 summarizes these findings. (Where: (a) is lecithin; (b) is sorbitan monooleate; (c) is octanoic acid; (d) is sodium octanoate; (e) is water; (f) is lidocaine; (g) is isopropyl myristate; and (v) microemulsion volume. Concentrations are expressed on a weight percentage basis (w/w).)

TABLE 7

Lecithin linker lidocaine Type I microemulsions with low lecithin content: formulation and lidocaine transdermal flux through excised pig ear skin.

| Series # | % (a) | % (b) | % (c) | % (d) | % (e) | % (f) | % (g) | (v), ml | Flux µg/cm² |
|---|---|---|---|---|---|---|---|---|---|
| Water      |     |      |     |      | 99.8 | 0.24 |      | 5.0 | 70 +/− 10 |
| LO-314-10  | 0.8 | 2.3  | 0.6 | 4.8  | 88.0 | 0.72 | 2.8  | 5.2 | 70 +/− 10 |
| LO-314-30  | 2.2 | 6.6  | 1.6 | 8.3  | 71.9 | 1.51 | 7.9  | 5.5 | 80 +/− 10 |
| LO-314-60  | 4.0 | 12.1 | 3.0 | 9.6  | 53.7 | 3.05 | 14.5 | 6.0 | 110 +/− 20 |
| LO-314-70  | 4.6 | 13.7 | 3.4 | 10.0 | 48.4 | 3.40 | 16.5 | 6.1 | 120 +/− 30 |
| LO-314-80  | 5.1 | 15.3 | 3.8 | 10.3 | 43.6 | 3.60 | 18.3 | 6.3 | 130 +/− 20 |
| LO-314     | 6.1 | 18.2 | 4.5 | 10.7 | 34.6 | 4.10 | 21.8 | 6.6 | 150 +/− 20 |

Example 8. Extended Release of Lidocaine with Type II Lecithin Linker Microemulsions In the previous examples, 0.4 mL of the donor solution is placed on the skin surface to provide continuous release of the drug. However, as indicated in Table 5, significant amount of lidocaine is absorbed when they are dosed in lecithin linker formulations. To test the ability of these formulations to provide extended release of lidocaine, three pieces of excised pig ear skin (0.74 cm diameter) were submerged in 5 mL of formulation LO-32 (Type II microemulsion, see Table 1) for 30 minutes. After this time, the pieces of skin were blotted with lint-free tissue to remove any excess liquid. The pieces of skin were assembled in MATTEK™ permeation devices to conduct extended release studies. The procedure was similar to that described in Example 5, with the exception that no donor solution was added and that the receiver solution was exchanged for fresh solution after 1, 2, 3, 6, 12, and 24 hr. FIG. 2 compares the accumulated mass of lidocaine permeated obtained for this extended release system to the ones obtained in the presence of a donor solution containing the same LO-32 formulation, and water saturated with lidocaine as donor solution. FIG. 3 indicates the fraction of lidocaine released from the skin (LO-32 extended release).

It will be appreciated by those skilled in the art that other variations of the preferred embodiment may also be practised without departing from the scope of the invention.

What is claimed is:

1. A microemulsion as a vehicle for delivery of an active ingredient, the microemulsion comprising:
   (a) a lecithin compound;
   (b) a lipophilic linker having an alkyl chain containing at least 12 carbon atoms and a hydrophilic-lipophilic balance (HLB) of about 5 or less, the lipophilic linker consisting of one or more ingredients selected from a group consisting of long chain alcohols, long chain fatty acids, monoglyceride, and sorbitan ester, the lipophilic linker being 0.1% to 24.0% w/w; and
   (c) a hydrophilic linker, the hydrophilic linker comprising an amphiphilic compound having an alkyl chain containing between 6 to 9 carbon atoms, the hydrophilic linker excluding $C_6$-$C_9$ alkyl glucosides and $C_6$-$C_9$ anionic alkyl sulfonates and with the proviso that when the hydrophilic linker comprises a carboxylic acid, said hydrophilic linker includes also a salt of said carboxylic acid, the hydrophilic linker being 0.1% to 24.0% w/w, wherein said microemulsion is free of polyethylene glycol, propylene glycol, short-chain alcohol and medium chain alcohol, and wherein the ratio of the lipophilic linker to the lecithin compound is between 1:1 and 3:1.

2. The microemulsion of claim 1 wherein the microemulsion is biocompatible and the delivery is topical, transdermal, oral, transnasal or intravenous.

3. The microemulsion of claim 1 wherein the microemulsion is water in oil (Type II) and topical or transdermal delivery produces an extended release profile.

4. The microemulsion of claim 1 wherein the lecithin compound is 0.1% to 8.0% w/w.

5. The microemulsion of claim 4 wherein the lecithin compound comprises at least 90% w/w of mono or di-alkyl phosphatidylcholines.

6. The microemulsion of claim 4 wherein the lecithin compound is obtained from animal, vegetable or chemical synthesis sources.

7. The microemulsion of claim 1 wherein the hydrophilic linker comprises C6-C9 fatty acids partially saponified.

8. The microemulsion of claim 1 wherein the hydrophilic linker is selected from phosphates, phosphonates, carboxylates, octanoates, neutralized C6-C9 carboxylic acids, alpha-hydroxy acids, esters of polyhydric alcohols, pyrrolidones, octanoic acid, 2-hydroxyoctanoic acid, octyl pyrrolidone, C6-C9 amines, quaternary ammonium salts, amine oxides, octylamine, C6-C9 alkyl aminopropionic acids, betaines, sulfobetaines, phosphatidylcholines, octyl sulfobetaine, dibutyryl phosphatidylcholine, or any combinations thereof.

9. The microemulsion of claim 1 wherein the hydrophilic linker is a mixture of octanoic acid and sodium octanoate.

10. The microemulsion of claim 1 further comprising a carrier oil, wherein the carrier oil is selected from terpenes or mixtures of diglycerides or triglycerides.

11. The microemulsion of claim 10 wherein carrier oil is 0-95% w/w.

12. The microemulsion of claim 1 wherein water is up to 90% w/w.

13. The microemulsion of claim 12 further comprising electrolytes to produce an isotonic formulation.

14. The microemulsion of claim 1 wherein the active ingredient is a drug having an aqueous solubility of less than 1% w/w in isotonic solutions at room temperature, and wherein the drug is soluble in a carrier oil.

15. The microemulsion of claim 1 wherein the hydrophilic linker is an ester of polyhydric alcohols.

16. The microemulsion of claim 1 wherein the lipophilic linker is a long chain alcohol.

17. The microemulsion of claim 1, wherein the lipophilic linker contains at least 18 carbon atoms.

18. The microemulsion of claim 17, wherein the lipophilic linker is from more than 2% w/w to about 24.0% w/w.

19. A method for manufacturing a microemulsion for controlling the delivery of an active ingredient, the method comprising:
   (a) forming a mixture free of polyethylene glycol, propylene glycol, short-chain alcohol and medium chain alcohol by mixing:
      (i) a lecithin compound;
      (ii) a lipophilic linker having an alkyl chain containing at least 12 carbon atoms and a hydrophilic-lipophilic balance (HLB) of about 5 or less, wherein the lipophilic linker consists of one or more ingredients selected from a group consisting of long chain alcohols, long chain fatty acids, monoglyceride, and sorbitan ester, the ratio of the lipophilic linker to the lecithin compound in the mixture being between 1:1 and 3:1; and
      (iii) a hydrophilic linker, wherein the hydrophilic linker comprises an amphiphilic compound having an alkyl chain containing between 6 to 9 carbon atoms, the hydrophilic linker excluding $C_6$-$C_9$ alkyl glucosides and $C_6$-$C_9$ anionic alkyl sulfonates, and with the proviso that when the hydrophilic linker comprises a carboxylic acid, said hydrophilic linker includes also a salt of said carboxylic acid;
   (b) dissolving the active ingredient into a carrier oil to form an active ingredient solution; and
   (c) mixing the mixture of step (a) with the active ingredient solution to form a microemulsion free of polyethylene glycol, propylene glycol, short-chain alcohol and medium chain alcohol.

20. The method of claim 19 wherein the delivery is topical, transdermal, oral, transnasal or intravenous.

21. The method of claim 19 wherein microemulsion is water in oil (Type II) and topical or transdermal delivery produces an extended release profile.

22. The method of claim 19 wherein the lipophilic linker is sorbitan monooleate, glycerol monooleate or oleic acid and wherein the hydrophilic linker is a mixture of octanoic acid and sodium octanoate.

23. The method of claim 19 wherein the carrier oil is alkyl esters of fatty acids, terpenes, or mixtures of monoglycerides, diglycerides or triglycerides.

24. The method of claim 19 wherein the microemulsion is an oil in water (Type I) and oral and intravenous delivery.

25. The method of claim 19 wherein the microemulsion is a bicontinuous microemulsion (Type III or IV) and topical transdermal, oral, transnasal or intravenous delivery.

26. A microemulsion as a vehicle for delivery of an active ingredient, the microemulsion comprising:
(a) a lecithin compound;
(b) a lipophilic linker, the lipophilic linker comprising an amphiphilic molecule having an alkyl chain with at least 12 carbons and a HLB of 5 or less, the lipophilic linker being selected from oleyl alcohol, cholesterol, lauric acid, palmitic acid, oleic acid, omega 6-fatty acids, omega 3-fatty acids, esters of these fatty acids with sorbitol, maltitol, xylitol, isomalt, lactitol, erythritol, pentaerythritol, glycerol, sorbitan monooleate, glycerol monooleate, or any combinations thereof; and
(c) a hydrophilic linker, the hydrophilic linker being from 0.1% to 24.0% w/w, wherein the hydrophilic linker comprises an amphiphilic compound having an alkyl chain containing between 6 to 9 carbon atoms, the hydrophilic linker excluding $C_6$-$C_9$ alkyl glucosides and $C_6$-$C_9$ anionic alkyl sulfonates,
wherein said microemulsion is free of polyethylene glycol free, propylene glycol, short-chain alcohol and medium chain alcohol, for delivery of the active ingredient from the microemulsion, and wherein the ratio of the lipophilic linker to the lecithin compound is between 1:1 and 3:1.

27. A method for controlling the delivery of an active ingredient, the method comprising:
(a) forming a mixture free of polyethylene glycol, propylene glycol, short-chain alcohol and medium chain alcohol mixture by mixing:
(i) a lecithin compound;
(ii) a lipophilic linker having an alkyl chain containing at least 12 carbon atoms and a HLB of 5 or less, the lipophilic linker selected from oleyl alcohol, cholesterol, lauric acid, palmitic acid, oleic acid, omega 6-fatty acids, omega 3-fatty acids, esters of these fatty acids with sorbitol, maltitol, xylitol, isomalt, lactitol, erythritol, pentaerythritol, glycerol, sorbitan monooleate, glycerol monooleate or any combinations thereof, the ratio of the lipophilic linker to the lecithin compound in the mixture being between 1:1 and 3:1; and
(iii) a hydrophilic linker, the hydrophilic linker comprising an amphiphilic compound having an alkyl chain containing between 6 to 9 carbon atoms, the hydrophilic linker excluding $C_6$-$C_9$ alkyl glucosides and $C_6$-$C_9$ anionic alkyl sulfonates;
(b) dissolving the active ingredient into a carrier oil to form an active ingredient solution;
(c) mixing the mixture of step (a) with the active ingredient solution to form a microemulsion; and
(d) delivering the microemulsion of step (c) to a subject.

28. A water in oil microemulsion as a vehicle for delivery of an active ingredient, the water in oil microemulsion comprising:
(a) a lecithin compound, said lecithin compound being from 2% to about 6% w/w;
(b) a lipophilic linker, wherein the lipophilic linker has an HLB of 5 or less and is a long chain alcohol, long chain fatty acids, monoglyceride, and sorbitan ester; and
(c) a hydrophilic linker, wherein the hydrophilic linker comprises an ester of polyhydric alcohols, the ester of polyhydric alcohol excluding $C_6$-$C_9$ alkyl glucosides and $C_6$-$C_9$ anionic alkyl sulfonates,
wherein said microemulsion is free of polyethylene glycol, propylene glycol, short-chain alcohol free and medium-chain alcohol, and wherein the ratio of the lipophilic linker to the lecithin compound is between 1:1 and 3:1.

29. A method of delivering agrochemicals through waxy cuticles of plant leaves, said method comprising contacting the plant leaves with a microemulsion, the microemulsion comprising: (a) a lecithin compound; (b) a lipophilic linker, the lipophilic linker consisting of one or more ingredients selected from a group consisting of long chain alcohols, long chain fatty acids, monoglyceride, and sorbitan ester, the lipophilic linker being 0.1% to 24.0% w/w; (c) a hydrophilic linker, the hydrophilic linker being an amphiphilic compound having an alkyl chain containing between 6 to 9 carbon atoms, the hydrophilic linker excluding $C_6$-$C_9$ alkyl glucosides and $C_6$-$C_9$ anionic alkyl sulfonates, and with the proviso that when the hydrophilic linker comprises a carboxylic acid, said hydrophilic linker includes also a salt of said carboxylic acid, the hydrophilic linker being 0.1% to 24.0% w/w, and (d) an agrochemical, and wherein the microemulsion is polyethylene glycol free, short-chain alcohol free and medium chain alcohol free.

* * * * *